United States Patent [19]
Bischof et al.

[11] Patent Number: 5,300,019
[45] Date of Patent: Apr. 5, 1994

[54] SYSTEMS AND METHODS FOR ERADICATING CONTAMINANTS USING PHOTOACTIVE MATERIALS IN FLUIDS LIKE BLOOD

[75] Inventors: Daniel F. Bischof, McHenry; Ludwig Wolf, Jr., Inverness; John T. Foley, Wheeling; William R. Bratten, Lake Villa, all of Ill.

[73] Assignee: Baxter International Inc., Deerfield, Ill.

[21] Appl. No.: 991,758

[22] Filed: Dec. 17, 1992

Related U.S. Application Data

[63] Continuation of Ser. No. 630,840, Dec. 20, 1990, abandoned.

[51] Int. Cl.$^5$ .............................................. A61F 2/38
[52] U.S. Cl. ................................. 604/4; 604/5; 604/20; 210/748
[58] Field of Search ............................ 604/4-6, 604/20; 210/748

[56] References Cited

U.S. PATENT DOCUMENTS

| | | |
|---|---|---|
| 2,308,516 | 1/1943 | Knott . |
| 4,181,128 | 1/1980 | Swartz . |
| 4,321,919 | 3/1982 | Edelson . |
| 4,398,906 | 8/1983 | Edelson . |
| 4,402,318 | 9/1983 | Swartz ........................ 604/20 |
| 4,428,744 | 1/1984 | Edelson . |
| 4,456,512 | 6/1984 | Bieler et al. .................... 210/748 |
| 4,573,962 | 3/1986 | Troutner . |
| 4,612,007 | 9/1986 | Edelson . |
| 4,613,322 | 9/1986 | Edelson . |
| 4,683,889 | 8/1987 | Edelson . |
| 4,684,521 | 8/1987 | Edelson . |
| 4,705,498 | 11/1987 | Goss . |
| 4,708,715 | 11/1987 | Troutner et al. . |
| 4,727,027 | 2/1988 | Wiesehahn et al. . |
| 4,737,140 | 4/1988 | Lee et al. . |
| 4,769,131 | 9/1988 | Noll et al. ..................... 210/748 |
| 4,775,625 | 10/1988 | Sieber . |
| 4,822,335 | 6/1989 | Kawai et al. . |
| 4,831,268 | 5/1989 | Fisch et al. . |
| 4,838,852 | 6/1989 | Edelson et al. ................. 604/4 |
| 4,878,891 | 11/1989 | Judy et al. . |
| 4,889,129 | 12/1989 | Dougherty et al. . |
| 4,915,638 | 4/1990 | Sieber . |
| 4,921,473 | 5/1990 | Lee et al. . |
| 4,944,883 | 7/1990 | Schoendorfer et al. ........... 210/782 |
| 4,950,225 | 8/1990 | Davidner et al. . |
| 4,983,307 | 1/1991 | Nesathurai .................... 210/748 |
| 5,030,200 | 7/1991 | Judy et al. ..................... 604/5 |
| 5,032,241 | 7/1991 | Robertson et al. .............. 210/748 |
| 5,069,885 | 12/1991 | Ritchie ......................... 210/748 X |
| 5,078,673 | 1/1992 | Abrams . |

FOREIGN PATENT DOCUMENTS 0138489 of 1984 European Pat. Off. .
92903137.5 7/1993 European Pat. Off. .

OTHER PUBLICATIONS

Matthews et al., "Photodynamic Therapy of Viral Contaminants with Potential for Blood Banking Applications", *Transfusion*, vol. 28,1 1988, pp. 81-83.

*Primary Examiner*—C. Fred Rosenbaum
*Assistant Examiner*—Corrine Maglione
*Attorney, Agent, or Firm*—Bradford R. L. Price; Paul C. Flattery; Daniel D. Ryan

[57] ABSTRACT

A system and method for treating a fluid carrying a biological contaminant to which a photoactive material has been bound include a treatment device that defines a flow passage with a gap. The system and method operate to establish a flow of fluid from the inlet end of the gap to the outlet end of the gap. The system and method expose the fluid, as it transits the gap, to a source of radiation that activates the photoactive material bound to the contaminant. The system and method also mix the fluid as it flows within the gap.

25 Claims, 8 Drawing Sheets

FIG. 14

SYSTEMS AND METHODS FOR ERADICATING CONTAMINANTS USING PHOTOACTIVE MATERIALS IN FLUIDS LIKE BLOOD This is a continuation of copending U.S. application Ser. No. 07/630,840 filed on Dec. 20, 1990 now abandoned.

FIELD OF THE INVENTION

The invention generally relates to the eradication of contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immuno-deficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components prior to storage and transfusion. See Matthews et. al., "Photodynamic Therapy of Viral Contaminants With Potential for Blood Bank Applications," Transfusion, 28(1), pp. 81-83 (1988). Various extracorporeal systems have been proposed that use photodynamic therapy to treat blood prior to storage and transfusion. See, for example, Edelson U.S. Pat. Nos. 4,613,322 and 4,684,521; Troutner et. al. U.S. Pat. No. 4,708,715; Wiesehahn et. al. U.S. Pat. No. 4,727,027; Sieber U.S. Pat. Nos. 4,775,625 and 4,915,683; and Judy et. al. U.S. Pat. No. 4,878,891.

To date, there has been a general lack of success in economically adapting the benefits of photodynamic therapy to the demands of the blood banking industry. The extracorporeal systems proposed to date have not been able to provide acceptable levels of eradication at the relatively high flow rates required to economically process therapeutic units of blood components.

For this and other reasons, the promise of photodynamic therapy in treating the nation's banked blood supply has gone largely unfulfilled.

SUMMARY OF THE INVENTION

The inventors have discovered that systems and methods can be provided that accommodate relatively high processing flow rates and yet achieve an acceptably high rate of contaminant eradication through photodynamic therapy.

The invention provides improved systems and methods for radiating a fluid carrying contaminants within a treatment chamber. According to the invention, the fluid is circulated in a purposeful manner within the chamber to bring the contaminants into direct exposure with the radiation.

A device that embodies the features of the invention includes an outer wall that defines an interior area. The outer wall is essentially transparent to radiation within a prescribed wavelength to thereby pass the radiation into the interior area. A treatment chamber is formed in the interior area for receiving the fluid to be treated. The fluid carries one or more contaminants to which a photoactive agent has been bound. The treatment chamber has an outer region that is adjacent the outer wall and an inner region that is spaced away from the outer wall. According to the invention, the device circulates the contaminants within the treatment chamber in a path that transports them away from the inner region and toward the outer region of the chamber. In this way, the contaminants are continuously being swept toward the transparent outer wall, where they can be most directly exposed to the radiation that activates the photoactive material.

A preferred system that embodies the features of the invention includes a housing having an interior rotor. The fluid gap exists between the interior wall of the housing and the exterior wall of the rotor. The system conveys through the gap the fluid carrying one or more contaminants to which a photoactive material has been bound. The system also transmits into the gap radiation to activate the photoactive material bound to the contaminants. At the same time, the system rotates the rotor inside the housing. The rotation creates vortices in the fluid transiting the gap. The vortices sweep the contaminants along in a helical path within the flow gap, keeping them continuously circulating in the radiation path. This mixing action assures that the contaminants are directly and uniformly exposured to radiation while transiting the gap.

In one arrangement, the system uses a single source of radiation positioned outside the housing. The system envelopes both the housing and the source with a reflective surface that focuses radiation from the source or sources into the housing.

In another arrangement, the system uses a number of discrete radiation sources. In one variation of this arrangement, the radiation sources are arranged in an array or bank at one end of an elliptical reflective surface. In this arrangement, the housing that encloses the treatment chamber is located at the other end of the elliptical reflective surface near a focal point. Radiation emitted by the radiation bank is thereby reflected uniformly into the flow gap.

In another variation of this arrangement, the radiation sources are themselves arranged as an envelope that surrounds the housing.

In a preferred embodiment, the multiple radiation sources comprise photodiodes.

A method that embodies the features of the invention conveys a fluid into a treatment chamber having an outer wall that is essentially transparent to radiation. The outer wall is exposed to a source of radiation. Contaminants present in the fluid are carried in a circulating flow path toward the outer wall for direct exposure to the radiation.

The systems and methods that embody the features of the invention are applicable for use in environments where sterility and biologically closed system integrity must be maintained during processing. The systems and methods therefore readily lend themselves to blood processing applications.

Other features and advantages of the invention will be pointed out in, or will be apparent from, the drawings, specification and claims that follow.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

Figure 1:
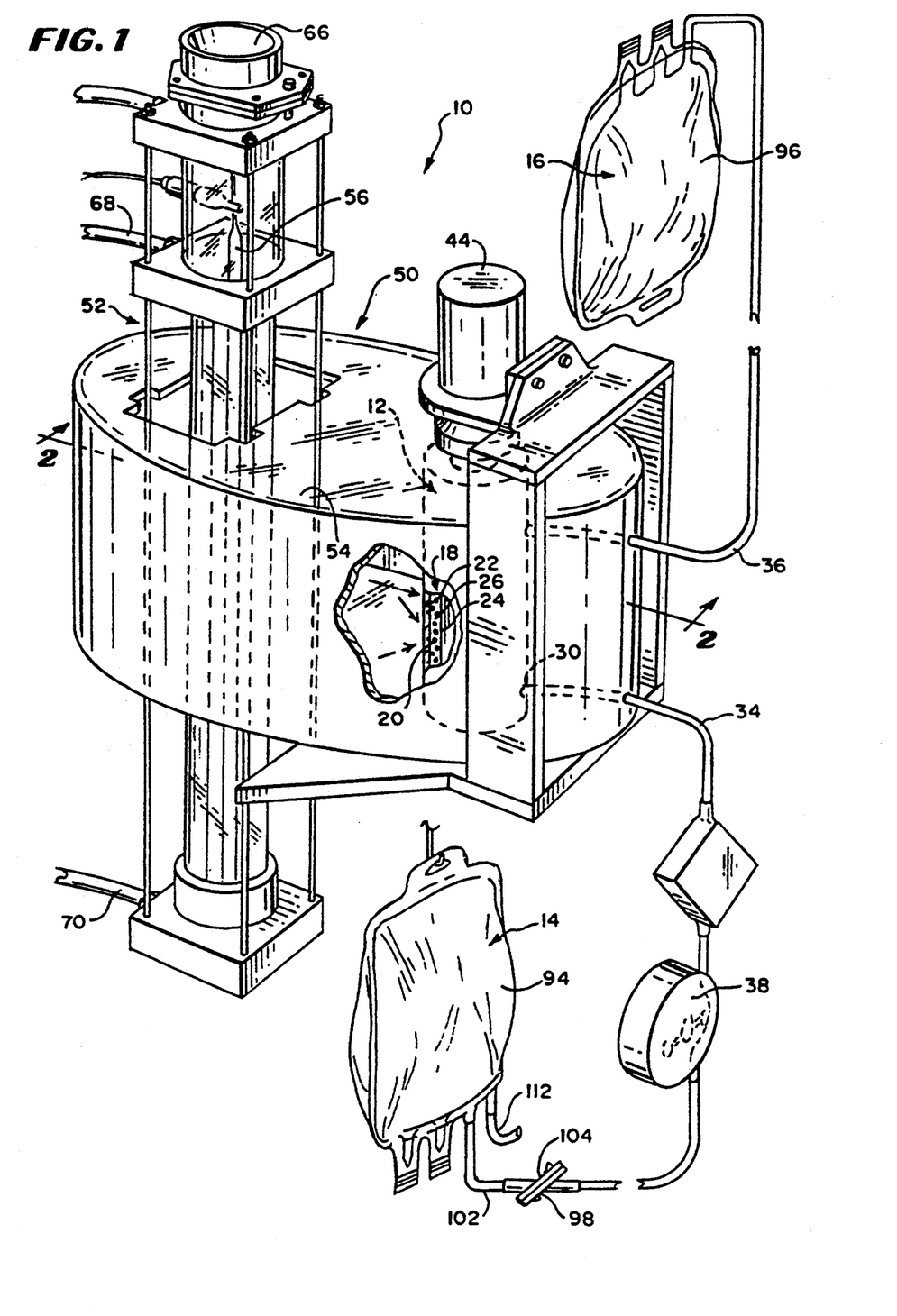
FIG. 1 is a perspective view, with portions broken away and in section of a system for treating fluids using photodynamic therapy that embodies the features of the invention.

FIG. 1 shows a system 10 for treating a fluid carrying a contaminant that embodies the features of the invention. The system 10 includes a treatment device 12 that receives the fluid from a source container 14 and conveys the fluid after treatment to a collection container 16.

The fluid to be treated can vary. In the illustrated embodiment, the fluid comprises a component of whole human blood that is intended to be stored for transfusion. More specifically, the fluid consists of red blood cells suspended in plasma. Typically, a quantity of white blood cells is also present with the red blood cells. The fluid can also include an anticoagulant and, optionally, a storage medium for the blood component. Alternatively, the fluid can consist of platelets suspended in plasma.

In the illustrated embodiment, the contaminant comprises a pathogenic virus typically carried in the blood. For example, the contaminant can consist of the hepatitis-B virus; the human immuno-deficiency virus; the Herpes virus; or the influenza virus.

The fluid in the source container 14 includes a photoactive material that has an affinity for the biological contaminant carried by the fluid. The photoactive material is added to the blood contained in the source container 14 after the blood is collected from a donor. The step of adding the photoactive material will be described in greater detail later.

Due to its affinity for the contaminant, the photoactive material becomes bound to the contaminant within the source container 14. The photoactive material is of a type that becomes active by exposure to radiation within a prescribed wavelength range. When activated by radiation, the material eradicates the contaminant.

Various types of photoactive materials can be used. In the illustrated embodiment, the photoactive compound comprises a family of light-activated drugs derived from benzoporphyrin. These derivatives are commonly referred as BPD's. BPD's are commercially available from Quadra Logic Technologies, Inc., Vancouver B.C., Canada.

BPD's, like other types of hematoporphyrin materials, have an affinity for the cell walls of many viral organisms that are carried in blood. They therefore bind or attach themselves to the biological cell wall of these organisms. When exposed to radiation, BPD's undergo an energy transfer process with oxygen, forming a singlet oxygen. When the singlet oxygen oxidizes, it kills the biological cells to which it has attached. BPD's are described in greater detail in Judy et. al. U.S. Pat. No. 4,878,891.

According to the invention, the treatment device purposefully agitates the fluid while exposing the contaminant to radiation.

Figure 2:
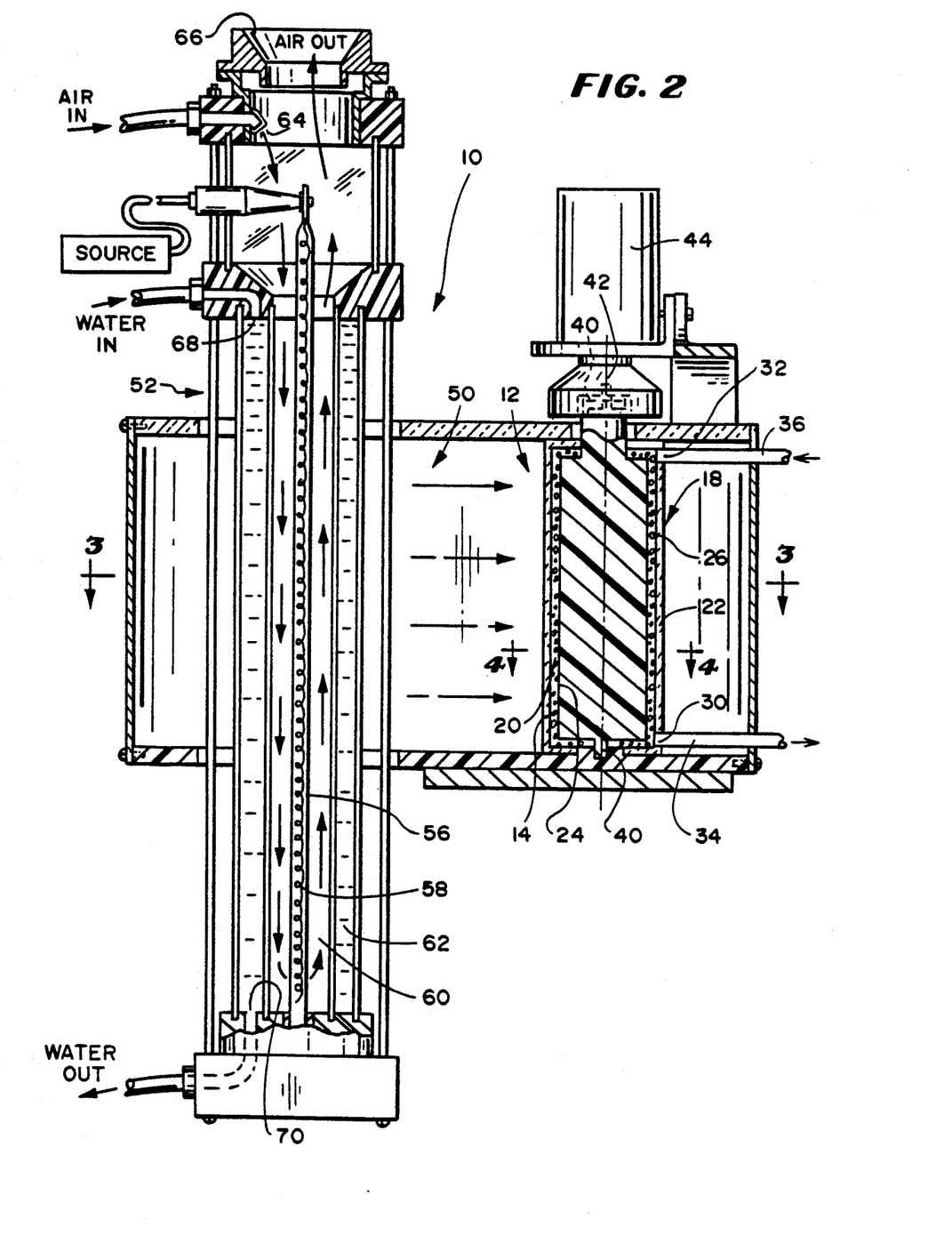
FIG. 2 is a side section view of the system shown in FIG. 1 taken generally along line 2—2 in FIG. 1.

As FIGS. 1 and 2 best show, the treatment device 12 includes a housing 18 that defines a treatment chamber 20. The housing 18 has a tubular outer wall 22.

The housing 18 also contains an interior wall 24. In the illustrated embodiment, the inner wall 24 takes the shape of a generally cylindrical rotor or spinner 24. A relatively narrow arcuate gap 26 exists between the rotor wall 24 and the interior of the housing wall 22. The arcuate gap 26 forms the confines of the treatment chamber 20.

In this arrangement (as FIGS. 4 and 5 best show), the treatment chamber 20 has an inner region 25 located along the rotor wall 24 and an outer region 23 located along the outer housing wall 22.

The housing wall 22 is made from a material that is essentially transparent to the radiation to thereby pass the radiation into the arcuate gap 26. This is shown by the arrow labeled with the letter R in FIGS. 4 and 5). The radiation passes first into the outer region 23 and then proceeds into the inner region 25, unless otherwise absorbed or reflected by matter present in the gap 26. Typically, the intensity of the radiation will diminish as it transits from the outer region 23 toward the inner region 25.

The fluid to be treated traverses the gap 26 between an inlet 30 and an outlet 32. The inlet 30 leads from the source container 14 through inlet tubing 34. The outlet 32 leads to the collection container 16 through outlet tubing 36. A pump 38 conveys fluid through the inlet tubing 34.

Bearings 40 carry the spinner 24 for rotation within the housing 18 about an axis 42 that is generally parallel to the direction of fluid flow in the gap 26 (see FIG. 2). A drive 44 magnetically coupled to the spinner 24 rotates the spinner 24 at a controlled surface velocity By rotating the spinner 24 as fluid traverses the gap 26, the flow patterns within the gap 26 are significantly altered. The rotating spinner 24 creates secondary fluid flow patterns called vortices 46 within in the gap 26 (see FIG. 5). The vortices 46 spiral in a helical path along the axis of rotation 42. These vortices 46 are sometimes referred in the technical literature to as "Taylor Vortices" (see Taylor, "Stability of a Viscous Liquid Contained Between Two Rotating Cylinders", *Proc. of the Royal Society*, V151 (1935), pp. 289–343).

Figure 5:
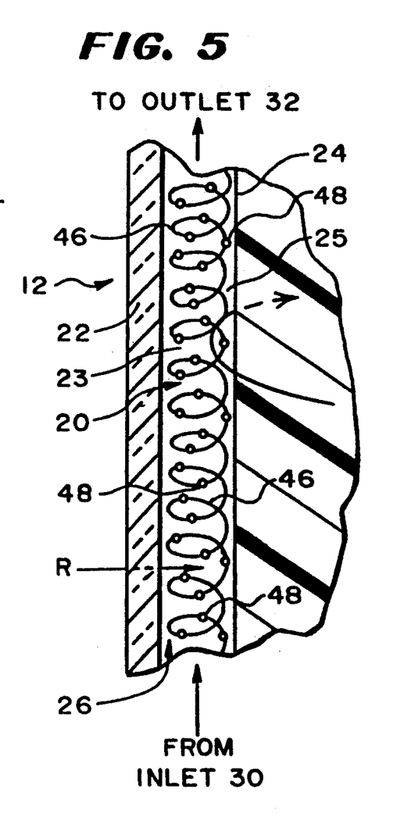
FIG. 5 is an enlarged side sectional view of the treatment chamber associated with the system shown in FIG. 1 taken generally along line 5—5 in FIG. 4.

As FIG. 5 shows, the vortices 46 continually sweep the material carried by the fluid, including the contaminants to which the photoactive agent are bound (generally designated by numeral 48 in FIG. 5) from the inner region 25 of the treatment chamber 20 toward the outer region 23. Thus, the contaminants 48 not only follow an axial path between the inlet 30 and outlet 32 of the gap 26, but the contaminants 48 also follow a radial, spiralling path through the gap 26. The vortices 46 continually keep the contaminants 48 in circulation near the outer housing wall 22, where the radiation enters the gap 26. These mixing patterns established by the vortices 46 assure that all contaminants 48 carried by the fluid are continuously brought to the outer region 23 where radiation first enter the treatment chamber 20 (that is, gap 26).

It should be appreciated that the vortices 46 shown in FIG. 5 can be created in alternate ways. For example, the housing 18 itself could be rotated about the spinner 24, which itself would remain stationary. This relative rotational movement between the housing 18 and the spinner 24 would create the same type of vortices 46 and lead to the same desirable mixing action.

The structural and operational relationships that govern the formation of the mixing vortices 46 shown in FIG. 5 are generally known. The axial value R (known as the axial Reynolds Number) is defined by the equation:

$$R = Vd/v,$$
where

V is the average axial velocity of the spinner 24;
d is the width of the gap 26; and
$v$ is the viscosity of the fluid being treated.

The value T (known as the Taylor Number) is defined by the equation:

$$T^2 = \Omega^2 r d^3 / v^2,$$
where
$\Omega$ is the angular velocity of the spinner 24;
r is the radius of the spinner 24; and
d and $v$ are as defined above.

If R is zero, a configuration shown in FIG. 5 will operate in four regimes:

(1) For low T values, the flow is of a laminar, Couette type.

(2) At a first threshold T value (typically about 41.3), the vortices 46 will develop without causing turbulence. As the T value increases above this first threshold value, the strength of the vortices will increase until a second threshold T value (typically about 400) is reached.

(3) Above the second threshold T value, the vortices 46 will continue, but turbulence will develop. The turbulence will increase until a third threshold T value (typically about 1715) is reached.

(4) Above the third threshold T value, the vortices 46 disappear, and the flow becomes purely turbulent.

The system 10 will achieve the objectives of the invention under flow conditions (2) and (3). The most preferred condition is (2).

Within the constraints established by these relationships, the size of the gap 26 and the surface velocity of the spinner 24 can be varied according to the type of fluid that is to be treated and the flow requirements of the treatment process.

In the illustrated embodiment, where the treated fluid contains blood materials, the gap 26 has a width of about 0.02 inch, and a length of about 3.0 inches. The spinner is rotated at about 3600 RPM's.

The treatment device 12 includes a radiation chamber 50 that directs radiation into the treatment chamber 20 (that is, into the gap 26). The radiation chamber 50 can be variously constructed. The drawings show three alternative constructions.

Figure 3:
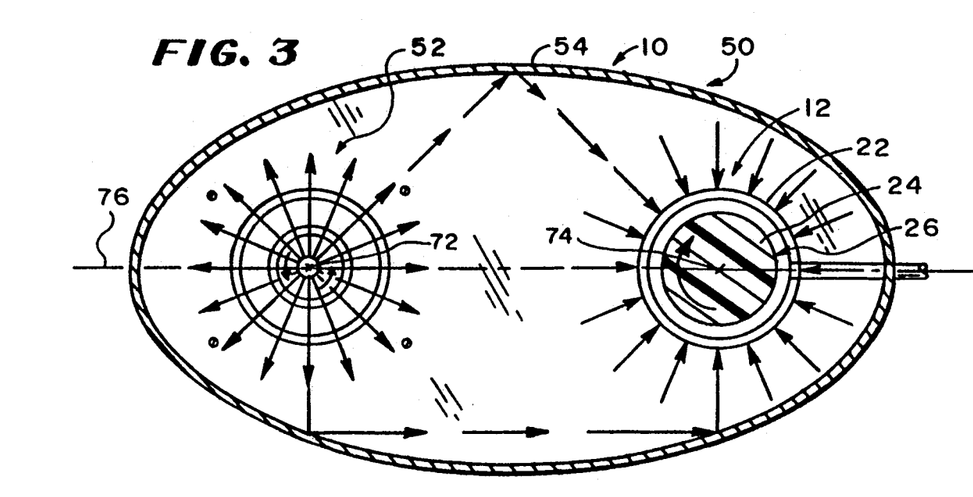
FIG. 3 is a top section view of the system shown in FIG. 1 taken generally along line 3—3 in FIG. 2.

In the embodiment shown in FIGS. 1 to 3, the radiation chamber 50 includes a single source of radiation 52 and a reflector 54 that envelopes both the radiation source 52 and the treatment device 12.

In this embodiment (as FIG. 2 best shows), the radiation source 52 comprises a tubular incandescent bulb 56 having an elongated filament 58. A power source (not shown) conveys electricity to the filament 58 to cause the filament 58 to emit radiation. The filament material is selected to emit radiation of a prescribed wavelength or range of wavelengths, according to the fluid that is to be treated.

In the illustrated embodiment, where the treated fluid contains red blood cells, filament 58 is made of tungsten. This material emits a band of radiation displaying a red color having a wavelength of about 690 nm. When operated at a voltage of about 250 volts (AC), the radiation emitted by the filament 58 has an intensity of about 1.7 mw/c$^2$.

Red blood cells are essentially transparent to radiation at this wavelength. The BPD's, however, are not. The BPD's absorb radiation in this wavelength to become activated.

On the other hand, if the fluid to be treated contains platelets, the filament would be selected to have a wavelength displaying a blue color having peak wavelength of about 425 nm. Platelets are essentially transparent to radiation at this wavelength, but the BPD's are not.

The incandescent source 52 shown in FIGS. 1 to 3 includes first and second chambers 60 and 62 that concentrically surround the bulb 56. Fluids are circulated through these chambers 60 and 62 to cool the radiation source.

In the arrangement shown in FIGS. 1 to 3, pressurized air circulates from an inlet 64 through the first chamber 60. The air is vented through a chimney 66 from the top of the first chamber 60. A secondary cooling liquid like water circulates from an inlet 68 at the top of the second chamber 62. The cooling liquid exits the second chamber 62 through a bottom outlet 70.

In embodiment shown in FIGS. 1 to 3, the reflector 54 is generally elliptical in shape (as FIG. 3 best shows). The elliptical reflector 54 has two diametrically spaced focal points positioned 72 and 74 along its major axis 76. The filament 58 of the radiation source 52 is located at one focal point 72. The rotational axis 42 of the spinner 24 within the treatment chamber 20 is located at the other focal point 74.

In this arrangement, the entire interior surface of the reflector 54 is lined with a material that reflects the radiation emitted by the source 52. Gold or like highly reflective material can be used to reflect the wavelengths of radiation described above.

Figure 4:
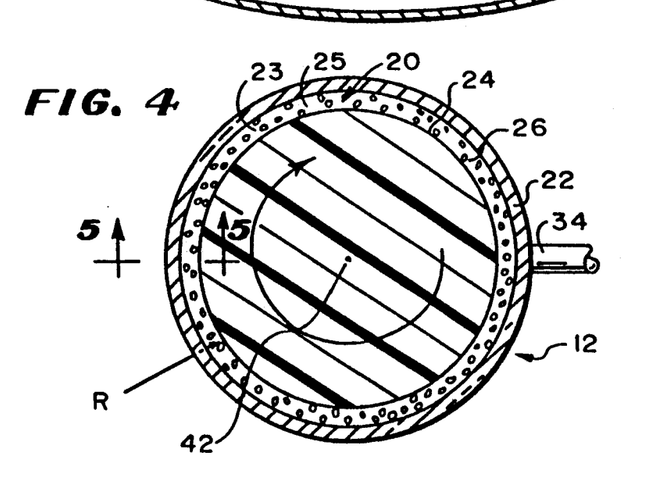
FIG. 4 is a top section view of the treatment chamber associated with the system shown in FIG. taken generally along line 4—4 in FIG. 2.

As FIG. 3 shows, the elliptical reflector 54 directs radiation emitted from the source uniformly around the exterior of the tubular housing 18 that surrounds the treatment chamber 20. Radiation uniformly fills the gap 26 of the treatment chamber 20 as the spinner 24 rotates to continuously mix the fluid as it traverses the gap 26 (as FIGS. 4 and 5 show).

In the second alternative embodiment (shown in FIGS. 6 to 9) the radiation chamber 50 includes a plurality of radiation sources (generally designated by the numeral 78). The treatment device 12 associated with this embodiment is the same as the one associated with the embodiment shown in FIGS. 1 to 3 (the interior of which in use is also shown in FIGS. 4 and 5).

In the illustrated embodiment (see FIGS. 6 and 9), each radiation source 78 is "discrete," meaning that each source 78 is a self-contained emitter of radiation that establishes its own zone of radiation. Being discrete, each source 78 also is capable of operation to emit a radiation independent of the emission of radiation by the other sources 78.

Figure 6:
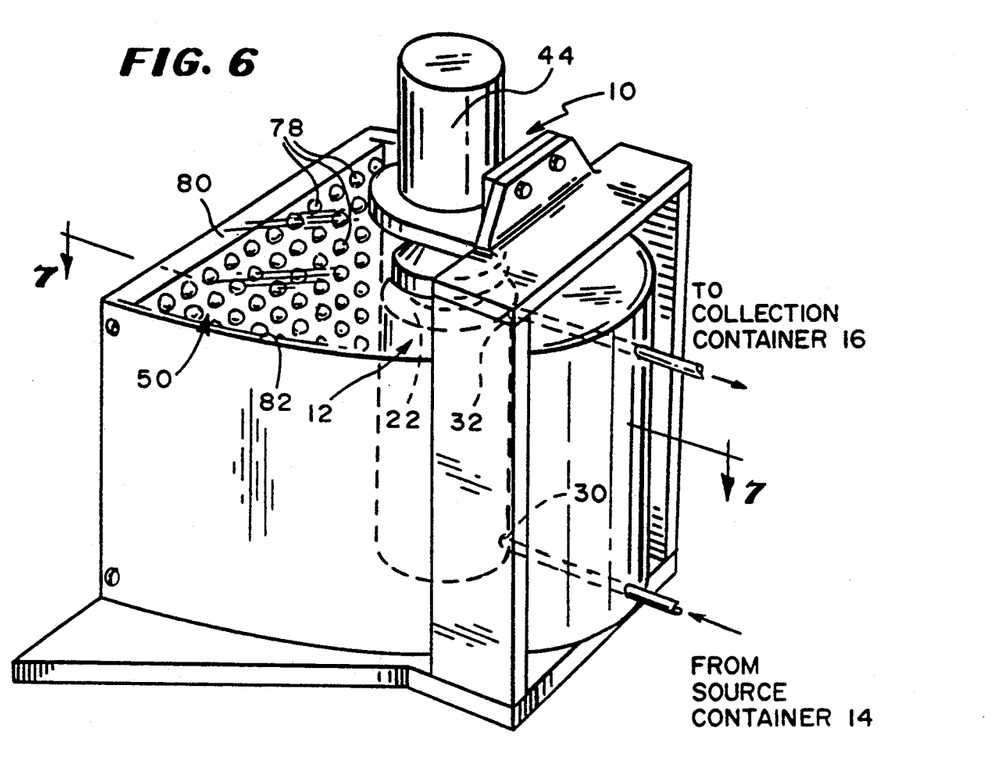
FIG. 6 is a perspective view of another system for treating fluids using photodynamic therapy that embodies the features of the invention.
Figure 9:
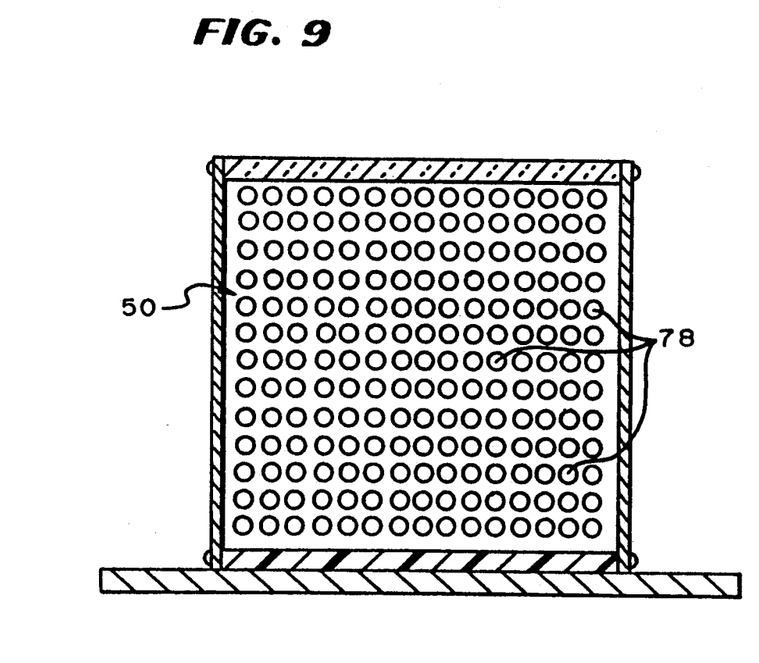
FIG. 9 is an elevation view of a portion of the system shown in FIG. 6 taken generally along line 9—9 in FIG. 8.
Figure 10:
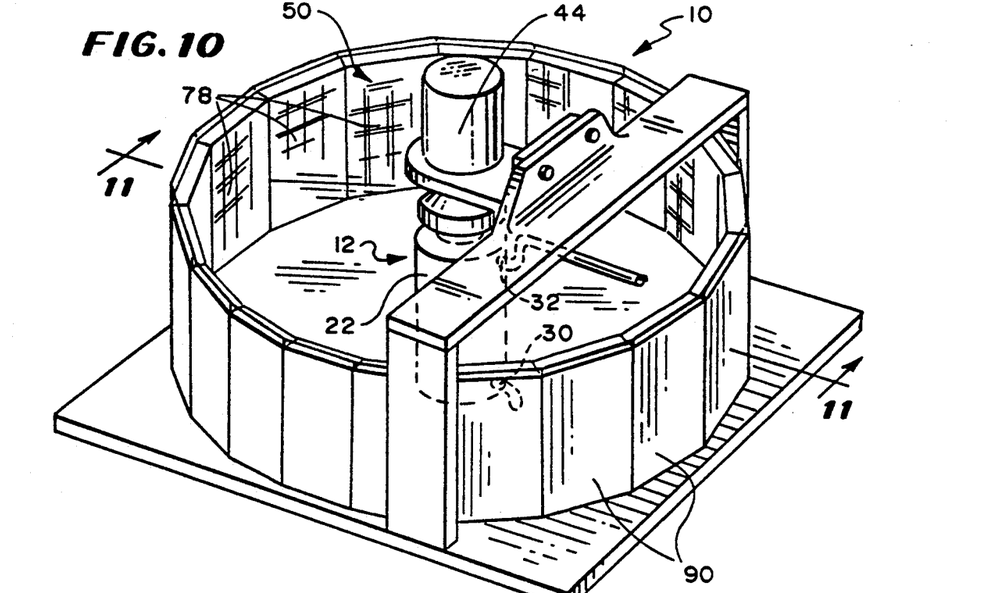
FIG. 10 is a perspective view of another system for treating fluids using photodynamic therapy that embodies the features of the invention.
Figure 11:
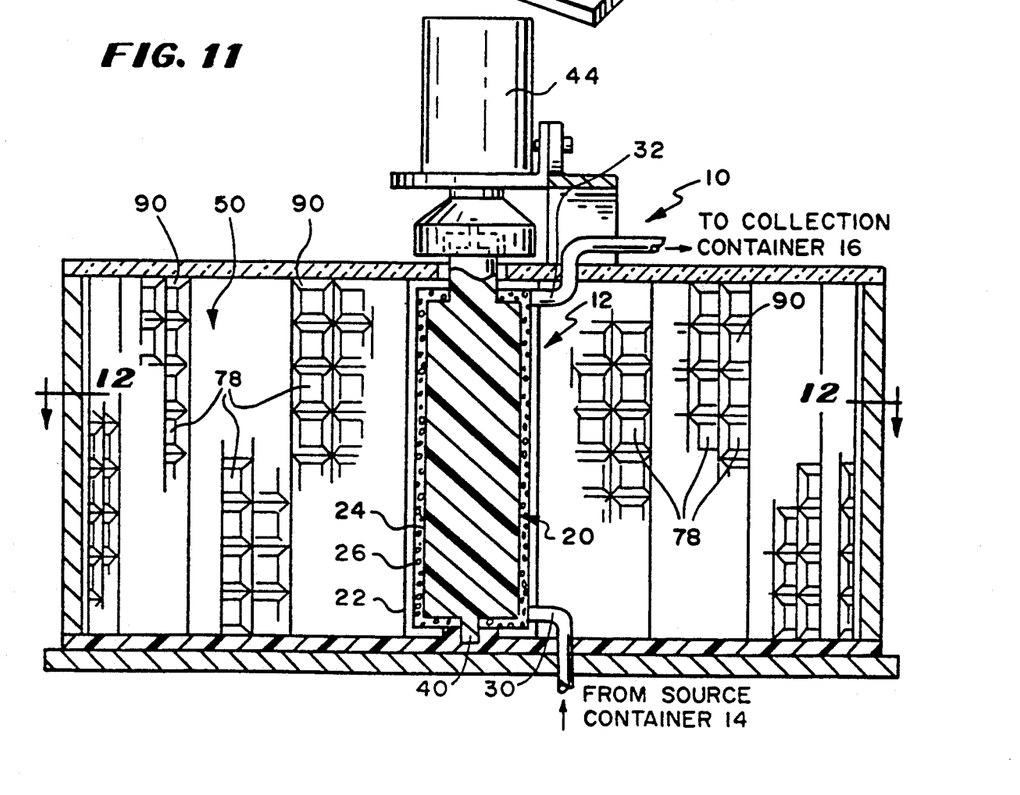
FIG. 11 is a side sectional view of the system shown in FIG. 10 taken generally along line 11—11 in FIG. 10.
Figure 12:
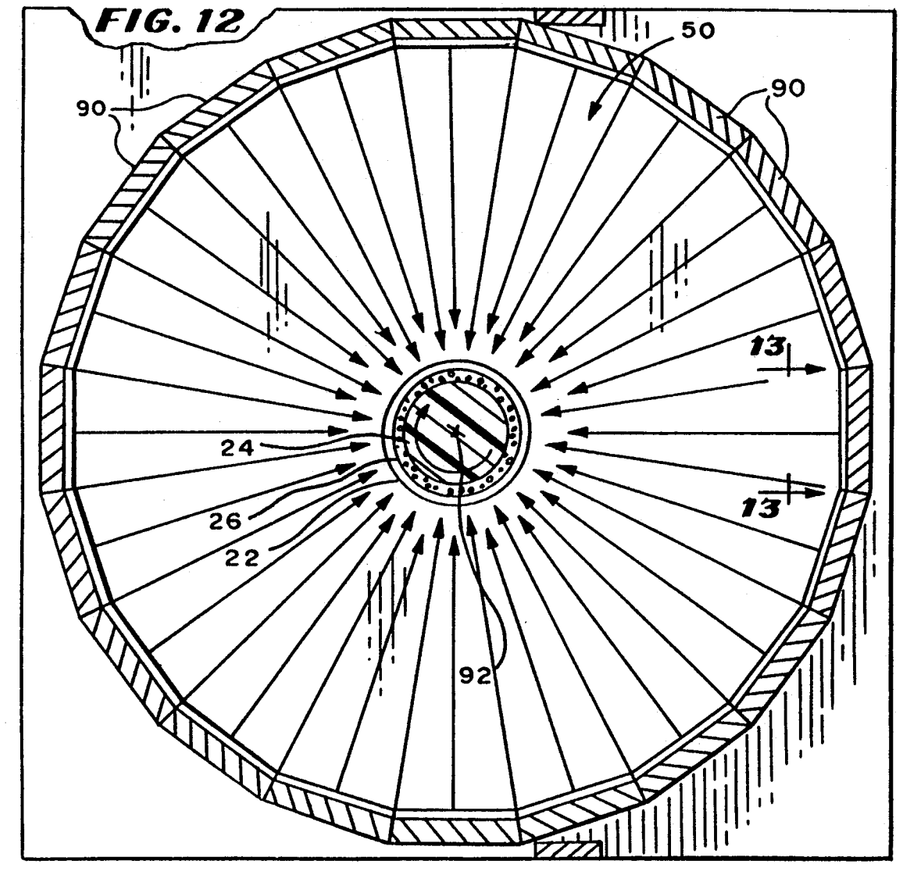
FIG. 12 is a top sectional view of the system shown in FIG. 10 taken generally along line 12—12 in FIG. 11.
Figure 13:
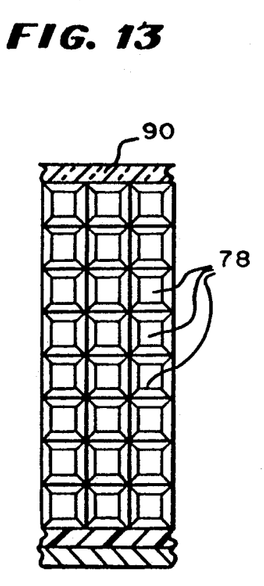
FIG. 13 is an elevation view of a portion of the system shown in FIG. 10 taken generally along line 13—13 in FIG. 12.

In the illustrated embodiment, each radiation source 78 takes the form of a photodiode. As with the single radiation source 52, various types of photodiodes can be selected, depending upon the fluid to be treated and the characteristics of the photoactive material used. In the illustrated embodiment, where the treated fluid contains red blood cells, all the photodiodes use transparent substrate aluminum gallium arsenide material (TS AlGaAs). Photodiodes of this type are commercially available from Hewlett-Packard Co. (Product Designation "HLMP-8150 15 Candella").

These photodiodes emit a band of radiation at a relatively narrow viewing angle of about 4 degrees. The prescribed band of radiation has a relatively precise wavelength displaying a red color having a peak wavelength of about 690 nm. As previously explained, if the fluid to be treated contains platelets, the photodiode would be selected to have a wavelength displaying a blue color having peak wavelenght of about 425 nm.

In the illustrated embodiment, each discrete photodiode radiation source 78 has a minimum intensity of about 8.0 cd (at 20 mA), a maximum intensity of about 36.0 cd (at 20 mA), and a typical intensity of about 15.0 cd (at 20 mA). Each photodiode source 78 operates at a low maximum forward voltage of about 2.4 V.

In embodiment shown in FIGS. 6 to 9, the discrete radiation sources 78 are arranged in a bank 80 (as FIG. 9 best shows). The bank 80 includes the plurality of discrete sources 78 arranged in rows of about 15 sources each (shown horizontally in FIG. 6). In the illustrated embodiment, the bank 80 includes about 195 discrete radiation sources 78. A control element (not shown) operates the discrete radiation sources 78.

In this arrangement, the radiation chamber 50 also includes a reflector 82 that surrounds the treatment chamber 20. As FIG. 7 best shows, the reflector 82 generally conforms to the shape of an ellipse that has been truncated along its minor axis 83 and therefore has but a single focal point 84. The bank 80 of radiation sources is located across the open end 86 the truncated reflector 82. The rotational axis 42 of the treatment chamber 20 is located at the closed end 88 along focal point 84.

Figure 7:
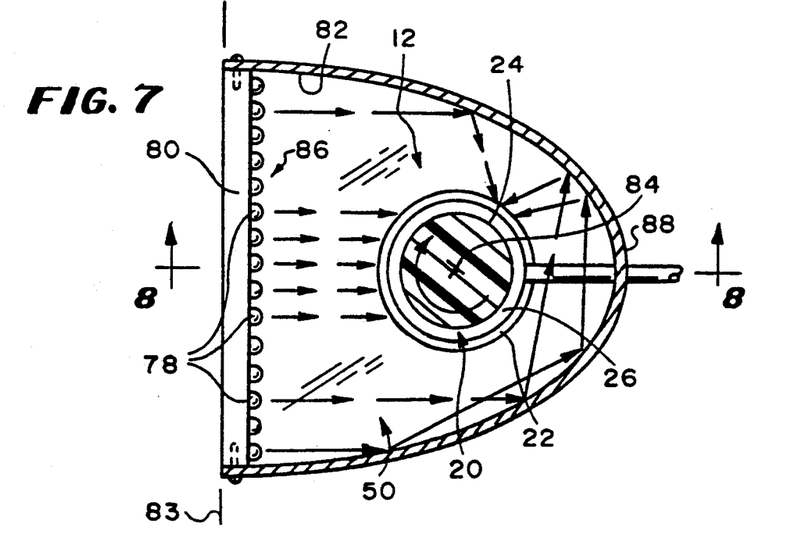
FIG. 7 is a top sectional view of the system shown in FIG. 6 taken generally along line 7—7 in FIG. 6.
Figure 8:
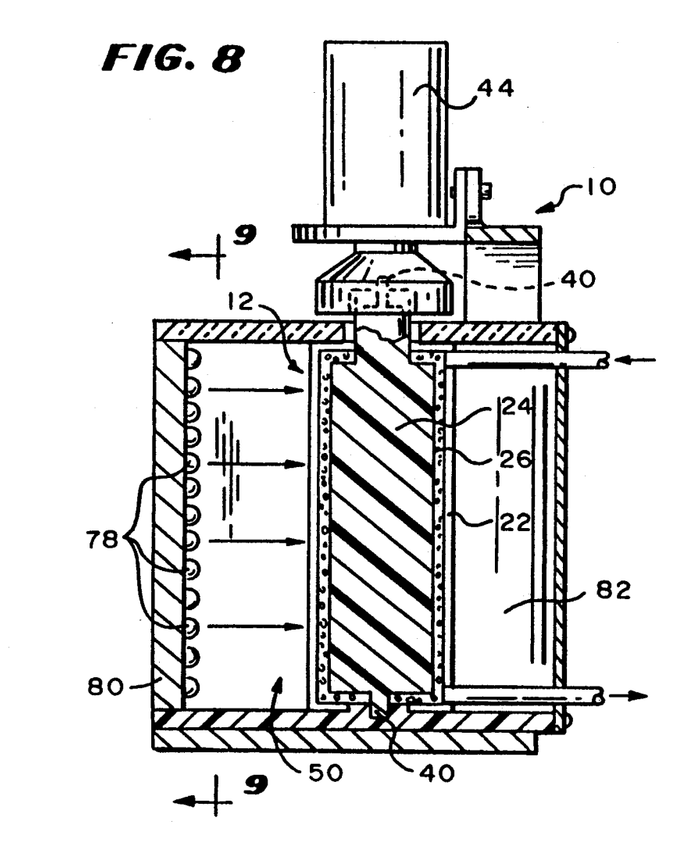
FIG. 8 is a side sectional view of the system shown in FIG. 6 taken generally along line 8—8 in FIG. 7.

As in the embodiment shown in FIGS. 1 to 3, the entire interior surface of the reflector 82 is lined with a material like gold that reflects the radiation emitted by the source. As FIG. 7 shows, the reflector 82 directs radiation emitted from the bank 80 uniformly around the exterior of the tubular housing 18 of the treatment chamber 20. Radiation uniformly fills the gap 26 of the treatment chamber 20 as the spinner 24 rotates to mix the fluid traversing the gap 26.

In the third alternative embodiment (shown in FIGS. 10 to 13), like the embodiment shown in FIGS. 6 to 9, the radiation chamber 50 includes a plurality of radiation sources that take the form of photodiodes (which are also generally designated by the same numeral 78). Like the embodiment shown in FIGS. 6 to 9, the discrete radiation sources 78 are arranged in individual banks 90. However, unlike the arrangement shown in FIGS. 6 to 9, the treatment chamber 20 does not include a reflector. Instead, the banks 90 of radiation themselves completely surround the treatment chamber 20.

In the illustrated embodiment, there are twenty (20) banks 90 arranged circumferentially about a center point 92. The rotational axis 42 of the treatment chamber 20 generally lies along on this center point 92. Each bank 90 includes twenty-four (24) discrete light sources 78. The treatment chamber 20 is thereby exposed to some 480 discrete radiation sources 78. A control element (not shown) operates the discrete radiation sources 78.

As in the preceding embodiments, the enveloping banks 90 of radiation sources 78 direct radiation uniformly around the exterior of the tubular housing 18 of the treatment chamber 20. Radiation uniformly fills the gap 26 of the treatment chamber 20 as the spinner 24 is rotated to mix the fluid traversing the gap 26.

Because each radiation source 78 shown in the second and third alternative embodiment is discrete, the control element can be configured to operate two or more of the radiation sources at a different wavelength. Alternatively, the control element can be configured to operate two or more of the discrete sources 78 of radiation at substantially the same wavelength.

Furthermore, the zone of radiation emitted by each discrete source 78 can be varied, as can the intensity of radiation of each source 78.

Figure 14:
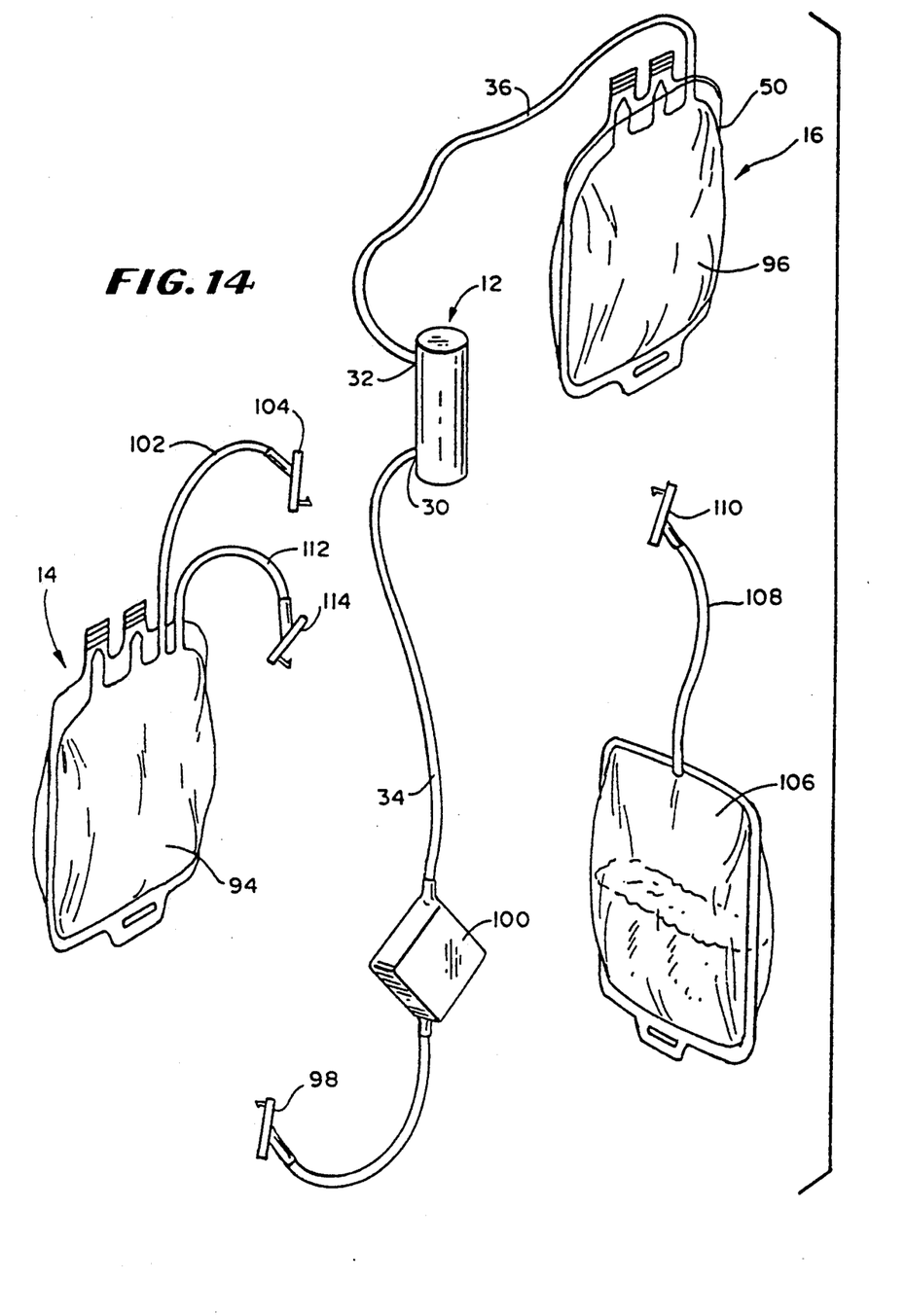
FIG. 14 is a perspective view of the treatment chamber and its associated components that the systems shown in FIGS. 1 to 13 incorporate, with the component disassembled as they would be prior to use.

In all the illustrated embodiments, the source container 14 and the collection container 16 each takes the form of a bag (respectively 94 and 96) made of a flexible inert plastic material, like plasticized medical grade polyvinyl chloride In the illustrated embodiment (as FIG. 14 shows), the inlet 30 to the treatment device 12 includes the length of flexible inert plastic tubing 34. The tubing 34 terminates in a first connection device 98. The tubing 34 also includes a conventional inline filter 100 for removing the white blood cells from the fluid prior to entering the treatment device 12. The filtration medium used (not shown) can include cotton wool, cellulose acetate, or another synthetic fiber like polyester.

A length of flexible inert plastic tubing 102 also joins the source container 14. This tubing 102 includes a second connection device 104 that mates with the first connection device 98 to join the source container 14 to the inlet 30 of treatment device 12 (as FIG. 1 shows).

While various known connection devices may be used, in the illustrated embodiment, the devices 98 and 104 are preferable sterile connection devices like those shown in Granzow et. al. U.S. Pat. Nos. 4,157,723 and 4,265,280, which are incorporated herein by reference.

The outlet 32 of the treatment device 12 also includes the already described tubing 36. The end of the tubing 36 joins the collection container 16. In an alternative arrangement (not shown), the tubing 36 could be normally separated into two lengths, like tubings 34 and 102, each having a sterile connection device to join the collection container 16 to the outlet 32 of the treatment device 12 prior to use.

In the illustrated embodiment (as FIG. 14 shows), an auxiliary container 106 holds a solution containing the photoactive material. The auxiliary container 106 also includes a length of tubing 108 that carries with a third (preferably sterile) connection device 110. In this arrangement, the source container 14 also includes another length of tubing 112 that carries a fourth (preferably sterile) connection device 114. By joining the third and fourth sterile connection devices 110 and 114, the photoactive material can be conveyed from the auxiliary container 106 into the source container 14 for mixing with the fluid to be treated. The joined tubings 108 and 112 form a closed, internally sterile path for introducing the photoactive materially into the source container 14. Once the photoactive material has been transferred, the tubing 108 can be heat sealed closed downstream of the joined connection devices 110 and 114 (as FIG. 1 shows), and the auxiliary container 106 removed.

By using the sterile connection devices 98, 104, 110, and 114, the formed flow paths comprise a closed, internally sterile path for conveying fluid from the source container 14, through the treatment chamber 20, and into the collection container 16.

After treatment, the tubing 36 can be heat sealed closed and the collection container 16 removed for storage.

The features and advantages of the invention are set forth in the following claims:

1. A device for treating a fluid carrying a contaminant to which a photoactive material has been bound, the material being activated by exposure to radiation within a prescribed wavelenght range to eradicate the contaminant, the device comprising
   an outer wall defining an interior area, the outer wall being essentially transparent to radiation within the prescribed wavelenght to pass the radiation into the interior area,
   an inner wall located within the interior area spaced from the outer wall,
   a treatment chamber formed in the interior area between the outer wall and the inner wall for receiving the fluid to be treated, the treatment chamber having an outer region adjacent the outer wall and an inner region adjacent the inner wall, and
   circulation means rotating the inner and outer walls relative to each other to create vortices in the fluid present within the treatment chamber that circulate the contaminant within the treatment chamber from the inner region toward the outer region for exposure to the radiation passing through the outer wall.

2. A device according to claim 1
   wherein the inner wall forms a rotor, and
   wherein the circulation means includes means for rotating the rotor within the interior area relative to the outer wall.

3. A device according to claim 1
   wherein the outer wall forms a generally tubular housing that peripherally defines the interior area,
   wherein the inner wall forms a generally cylindrical member located within the housing, the space between the inner wall and the outer wall forming an annular gap that comprises the treatment chamber, and
   wherein the circulation means includes means for rotating the cylindrical member and outer wall relative to each other to create vortices within the annular gap to circulate the contaminant toward the outer region of the annular gap.

4. A device according to claim 1
   wherein the annular gap includes an inlet for receiving fluid and an outlet for discharging fluid, the inlet and outlet being spaced relative to the axis of rotation.

5. A device according to claim 4
   wherein the cylindrical member comprises a rotor, and
   wherein the circulation means includes means for rotating the rotor within the interior area relative to the outer wall.

6. A system for treating a fluid carrying a contaminant to which a photoactive material has been bound, the material being activated by exposure to radiation within a prescribed wavelenght range to eradicate the contaminant, the system comprising
   a treatment device including
      an outer housing wall defining an interior area, the outer wall being essentially transparent to radiation within the prescribed wavelenght to pass the radiation into the interior area,
      an inner wall in the interior area spaced from the outer wall, the space between the inner and outer wall defining a treatment chamber for receiving the fluid to be treated for exposure to radiation passing through the outer wall, and
      circulation means for rotating the inner and outer walls relative to each other to create vortices that circulate the contaminant present within the treatment chamber from the inner wall toward the outer wall, and
   means for emitting radiation within the prescribed wavelenght range through the outer housing wall and into the treatment chamber to activate the photoactive material bound to the contaminant.

7. A system according to claim 6
   wherein the radiation emission means is spaced from the treatment device and includes means for focusing the emitted radiation through the outer housing wall.

8. A system according to claim 6
   wherein the inner wall forms a rotor, and
   wherein the circulation means includes means for rotating the rotor within the interior area to create vortices that circulate the contaminant present within the treatment chamber from the inner wall toward the outer wall.

9. A system according to claim 6
wherein the outer wall forms a generally tubular housing that peripherally defines the interior area,
wherein the inner wall forms a generally cylindrical rotor located within the housing, the treatment chamber comprising an annular gap in the space between the inner wall and the outer wall, and
wherein the circulation means includes means for rotating the rotor and the outer wall relative to each other to create vortices within the annular gap that circulate the contaminant from the inner wall toward the outer wall.

10. A system according to claim 9
wherein the circulation means includes means for rotating the rotor within the interior area to create the vortices within the annular gap.

11. A system according to claim 9
wherein the gap includes an inlet for receiving fluid and an outlet for discharging fluid, the inlet and outlet being spaced apart relative to the axis of rotor rotation,
and further including means for conveying fluid through the gap from the gap inlet to the gap outlet.

12. A system according to claim 6
wherein the radiation emission means includes a single source of radiation.

13. A system according to claim 6
wherein the radiation emission means includes multiple sources of radiation.

14. A system according to claim 13
wherein each multiple radiation source is discrete.

15. A system according to claim 6
wherein the radiation emission means includes a photodiode.

16. A system according to claim 6 wherein the radiation emission means includes a source of radiation and a reflective surface that surrounds at least a portion of the treatment device.

17. A system according to claim 16
wherein the reflective surface is elliptical in shape.

18. A system according to claim 17
wherein the elliptical reflective surface includes diametrically spaced first and second focal points,
wherein the source of radiation is located at one of the focal points, and
wherein the treatment device is located at the other focal point.

19. A system according to claim 17
wherein the elliptical reflective surface includes an open end extending along its minor axis and closed end spaced from the open end and including a focal point,
wherein the source of radiation is located at the open end of the ellipse and faces in the direction of the closed end, and
wherein the treatment device is located in the closed end at focal point.

20. A system according to claim 6
wherein the radiation emission means includes multiple sources of radiation that peripherally surround the treatment device.

21. A system according to claim 20
wherein the multiple sources of radiation include photodiodes.

22. A method for treating a fluid carrying a contaminant to which a photoactive material has been bound, the material being activated by exposure to radiation within a prescribed wavelenght range to eradicate the contaminant, the method comprising the steps of
conveying the fluid through a gap formed between an outer wall and an inner wall, the outer wall being essentially transparent to radiation within the prescribed wavelength, and
exposing the fluid, as it transits the gap, to a source of radiation that passes through the outer wall while rotating the inner and outer walls relative to each other to create vortices that circulate the contaminant within the gap toward the outer wall for exposure to the radiation.

23. A method according to claim 22
wherein, during the radiation exposure step, the inner wall is rotated relative to the outer wall.

24. A method for treating a fluid containing a blood component and a biological contaminant comprising the steps of
adding a photoactive material to the fluid that binds itself to the contaminant, the material being activated by exposure to radiation within a prescribed wavelength range to eradicate the contaminant,
conveying the fluid through a gap formed between an outer wall and an inner wall, the outer wall being essentially transparent to radiation within the prescribed wavelength, and
exposing the fluid, as it transits the gap, to a source of radiation that passes through the outer wall while rotating the inner and outer walls relative to each other to create vortices that circulate the contaminant within the gap toward the outer wall for exposure to the radiation.

25. A method according to claim 28
wherein, during the radiation exposure step, the inner wall is rotated relative to the outer wall.

* * * * *

UNITED STATES PATENT AND TRADEMARK OFFICE
CERTIFICATE OF CORRECTION

PATENT NO. : 5,300,019

DATED : April 5, 1994

INVENTOR(S) : Daniel F. Bischof, et al.

It is certified that error appears in the above-identified patent and that said Letters Patent is hereby corrected as shown below:

In claim 1, at column 9, lines 54 and 58, delete "wavelenght" and substitute -- wavelength -- therefor.

In claim 1, at column 9, line 67, after "means", insert --for--.

In claim 4, at column 10, line 24, delete "claim 1" and substitute --claim 3-- therefor.

In claim 6, at column 10, lines 38, 43 and 56, delete "wavelenght" and substitute --wavelength-- therefor.

In claim 22, at column 12, line 18, delete "wavelenght" and substitute --wavelength-- therefor.

UNITED STATES PATENT AND TRADEMARK OFFICE
CERTIFICATE OF CORRECTION

PATENT NO. : 5,300,019

DATED : April 5, 1994

INVENTOR(S) : Daniel F. Bischof, et. al.

It is certified that error appears in the above-indentified patent and that said Letters Patent is hereby corrected as shown below:

In claim 25, at column 12, line 50, delete "claim 28" and subsitutue-- claim 22-- therefor.

Signed and Sealed this

Fourteenth Day of February, 1995

Attest:

BRUCE LEHMAN

Attesting Officer

Commissioner of Patents and Trademarks